United States Patent
Burnett

(10) Patent No.: US 6,884,988 B2
(45) Date of Patent: Apr. 26, 2005

(54) AUTOMATED OPTICAL INSPECTION SYSTEM WITH LIGHT TRAP

(75) Inventor: John B. Burnett, Vacaville, CA (US)

(73) Assignee: Landrex Technologies Co., Ltd., Taipei-Hsien (TW)

( * ) Notice: Subject to any disclaimer, the term of this patent is extended or adjusted under 35 U.S.C. 154(b) by 16 days.

(21) Appl. No.: 10/026,396

(22) Filed: Dec. 21, 2001

(65) Prior Publication Data

US 2003/0116727 A1 Jun. 26, 2003

(51) Int. Cl.[7] .............................. H01J 3/14; H01J 40/14; H01J 5/16
(52) U.S. Cl. .................. 250/216; 250/559.45; 359/629; 356/237.4
(58) Field of Search ............................ 250/216, 559.45, 250/559.46; 348/126; 359/629–630; 356/237.4–237

(56) References Cited

U.S. PATENT DOCUMENTS

| | | | | | |
|---|---|---|---|---|---|
| 5,170,063 A | * | 12/1992 | Miyazaki et al. | ...... | 250/559.45 |
| 6,069,690 A | * | 5/2000 | Xu et al. | ...... | 356/73 |
| 6,191,850 B1 | * | 2/2001 | Chiang | ...... | 356/237.4 |

FOREIGN PATENT DOCUMENTS

EP 760486 A1 * 3/1997 ............ G02B/5/00

* cited by examiner

Primary Examiner—Stephone B. Allen
Assistant Examiner—Patrick J. Lee
(74) Attorney, Agent, or Firm—MacPherson Kwok Chen & Heid LLP

(57) ABSTRACT

An automated optical inspection system with improved accuracy achieved by reducing the negative effects of extraneous light. The system includes a light trap behind a two-way mirror.

17 Claims, 5 Drawing Sheets

AUTOMATED OPTICAL INSPECTION SYSTEM WITH LIGHT TRAP

This invention relates generally to automated optical inspection and more specifically to equipment for improved inspection accuracy.

Automated optical inspection (AOI) is used in many fields, particularly in the manufacture of electronic assemblies, such as printed circuit boards. Such a system generally includes a light source, a camera that makes an image of the article being inspected and a computer connected to the camera to process the image.

The computer detects the presence or absence of features in the image. A circuit board might be declared as good if the computer detects all the components that should be on the printed circuit board in their expected places. Conversely, a board might be declared as faulty if the computer either fails to detect some of the components or identifies objects that should not be present on a properly assembled printed circuit board.

In an automated optical inspection system, the relative position of the light source and the camera is usually selected to ensure that the components on the boards are highlighted in the image. For example, when an AOI system is inspecting for the presence of parts packaged in plastic packages, the light source and the camera are often separated by a relatively large angle. Lighting the parts from the same angle they are inspected from often provides insufficient visual contrast between the part and the printed circuit board, making it difficult to determine whether the part is present.

On the other hand, when the part being inspected is a shiny metal pad, directing light onto the component from directly above the circuit board and also inspecting from that angle can produce an image with a large contrast between the pad and the circuit board, making inspection more reliable. It is difficult to provide a system with both an illumination and an inspection angle that are the same because that requires having the light source and the camera occupy the same space. In prior art systems, such an illumination angle has been achieved with a device known as a beam splitter.

FIG. 1 illustrates a prior art AOI system 100 configured for top lighting, here shown inspecting a printed circuit board 102. Components 104 are on the surface of the board. Camera 112 is mounted above the board. One of skill in the art will appreciate that the illustrated components are mounted in a housing or other convenient support structure. Further, AOI system 100 would have a conveyor or similar components to move circuit board 102 relative to camera 112. However, the exact details are not illustrated for simplicity and are not important for the invention.

Light source 106 provides the source of illumination. Light source 106 emits light in the direction shown by arrow 1. Arrow 1 is at a right angle to the optical axis of camera 112. To align the light from source 106 with the optical axis of camera 112, beam splitter 108 is used.

Beam splitter 108 is a conventional part. A suitable device might, for example, be purchased from Edmond's Scientific company. Beam splitter 108 includes a two-way mirror 110. Mirror 110 is mounted at approximately a 45 degree angle relative to arrow 1. Mirror 110 reflects the light from source 106 towards printed circuit board 102. After reflection, the source light travels in the direction indicated by arrow 2.

Incident light is reflected from the component 104 under inspection. Some part of the incident light is reflected upwards towards camera 112, as shown by arrow 3. Mirror 110 is a two-way mirror, meaning it has a reflection coefficient that differs based on the incident angle of the light. It has a high reflection coefficient for light impinging on the mirror from direction 1, but a very low coefficient of reflection for light impinging from direction 3. Mirror 110 largely passes, rather than reflecting, light impinging from direction 3.

Thus, light reflected from component 104 being inspected, passes to camera 112. In this way, the incident light arrives at the component 104 from a direction that is along the optical axis of camera 112.

We have discovered a drawback of using a beam splitter to align the light source with the optical axis of the camera. Two way mirror 110 can not be made perfectly reflective. Some portion of the incident light is transmitted through mirror 110, traveling in the direction of arrow A. While the inside of beam splitter 108 is black, it is sufficiently reflective that some of the light traveling in direction A will reflect from the wall of beam splitter 108 and be reflected back towards mirror 110, traveling in the direction of arrow B.

This reflected light, upon reaching mirror 110, is reflected in the direction of arrow C, which directs the light to camera 112. Thus, in addition to receiving light which represents the image of the board being inspected, camera 112 also receives extraneous light that has passed through mirror 110 and been reflected. We recognized that this extraneous light creates a "shadow image" of light source 106 in the image passed to computer 116 for processing. In some instances, the shadow image has been bright enough to "confuse" the computer 116 into reporting the presence of an unwanted component on printed circuit board 102 or reporting that a needed component is not in its intended location.

SUMMARY OF THE INVENTION

With the foregoing background in mind, it is an object of the invention to provide an AOI system with improved accuracy.

The foregoing and other objects are achieved through the use of a beam splitter with a light trap to reduce the impact of a shadow image.

According to a preferred embodiment, the light trap is mounted behind a two-way mirror in a beam splitter.

Also according to the preferred embodiment, the light trap includes an angled surface an light absorbing material.

BRIEF DESCRIPTION OF THE DRAWINGS

The invention will be better understood by reference to the following more detailed description and accompanying drawings in which.

DESCRIPTION OF THE PREFERRED EMBODIMENT

Figure 1:
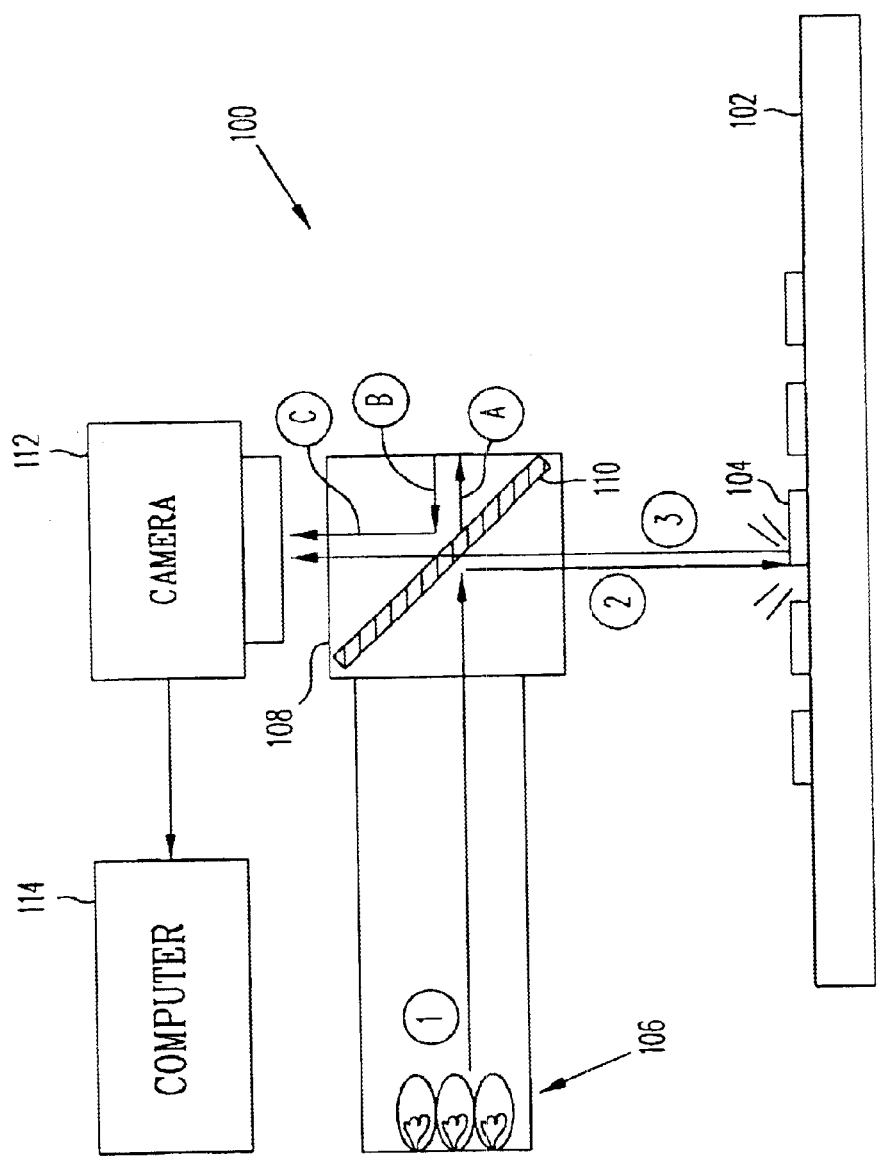
FIG. 1 is a sketch illustrating a prior art top-lighted AOI system.
Figure 2:
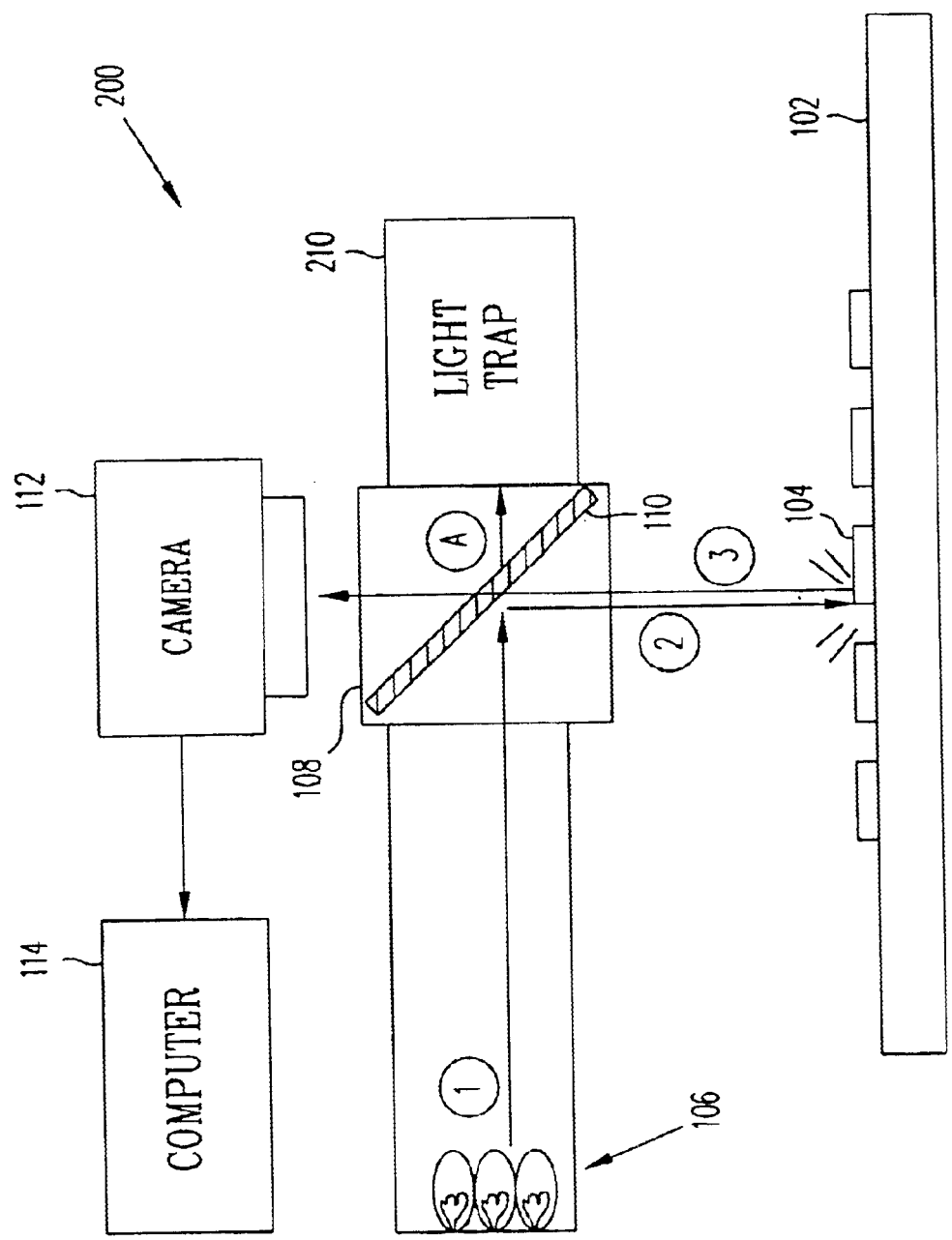
FIG. 2 is a sketch illustrating a top-lighted AOI system employing the invention.

FIG. 2 shows a top lighted AOI system 200. AOI system resembles the prior art AOI system of FIG. 1, but includes light trap 210 attached to beam splitter 108. Light trap 210 receives extraneous light passing through mirror 110 and substantially reduces any reflection back towards mirror 110. In this way, the shadow image problem of the prior art is substantially eliminated.

In a preferred embodiment, beam splitter 108 is purchased with multiple ports to which light sources, cameras or other devices might be attached. When not in use, the ports are covered with plugs. Thus, one simple way to attach light trap 210 to beam splitter 108 is to simply remove the plug and attach light trap 210 with screws or other fasteners that are compatible with the design of beam splitter 108.

Turning to FIG. 3, details of light trap 210 are shown. FIGS. 3A to 3C shown alternative implementations of a light trap. In FIG. 3A, a light trap 210A is shown to include a cylinder 310 with a cone 312 inside. There is open space between the inner walls of cylinder 310 and outer surface of cone 312, forming a "chamber" 313.

Extraneous light enters the cylinder 310 in direction A. Cone 312 presents an angled surface that reflects the extraneous light in a direction away from direction A. As shown in the FIG. 3A, the reflected light is directed toward the interior walls of cylinder 310. The light continues to be reflected between the exterior surface of cone 312 and the interior walls of cylinder 310, staying within chamber 313. At each reflection, the light is attenuated. After a sufficient number of reflections, the light is dissipated.

Preferably the outer surface of cone 312 and the inner walls of cylinder 310 are made of a light absorptive material. The material should also provide very little back scattering of the light. In this way, the amount of light leaving light trap 210 is so small that it has no practical effect on AOI system 200.

A suitable material for constructing light trap 210 is black anodized aluminum. This material is preferred because of its absorptive properties and because it has sufficient strength to be machined. However, other suitable materials might be employed. Including cloth or paper covering other materials to achieve the required strength to be formed into the desired shapes.

FIG. 2B shows an alternative embodiment of light trap 210B. Light trap 210B includes an outer cylinder 314 and an inner cylinder 316 and a cone 318. Cylinders 314 and 316 are concentric, creating a space or "chamber" between the inner walls of cylinder 314 and the outer walls of cylinder 316. Inner cylinder 316 has a slit 320 formed around it, creating an opening into space 322.

Extraneous light enters light trap 210B traveling in the direction A. Cone 318 has an outer surface shaped to reflect light traveling in direction A towards slit 320. In a preferred embodiment, the outer surface of cone 318 is parabolic. In this way, extraneous light is diverted into chamber 322. Though not explicitly shown in FIG. 3B, space 322 is sealed with a wall at the end facing beam splitter 108. In this way, extraneous light becomes trapped in chamber 322 and is not reflected back towards mirror 110. In the preferred embodiment, the inner wall of cylinder 314, the outer wall of cylinder 316 and the outer surface of cone 318 are made of light absorptive material, such as black anodized aluminum. In this way, extraneous light dissipates as it is reflected from the walls in chamber 322.

Figure 3B:
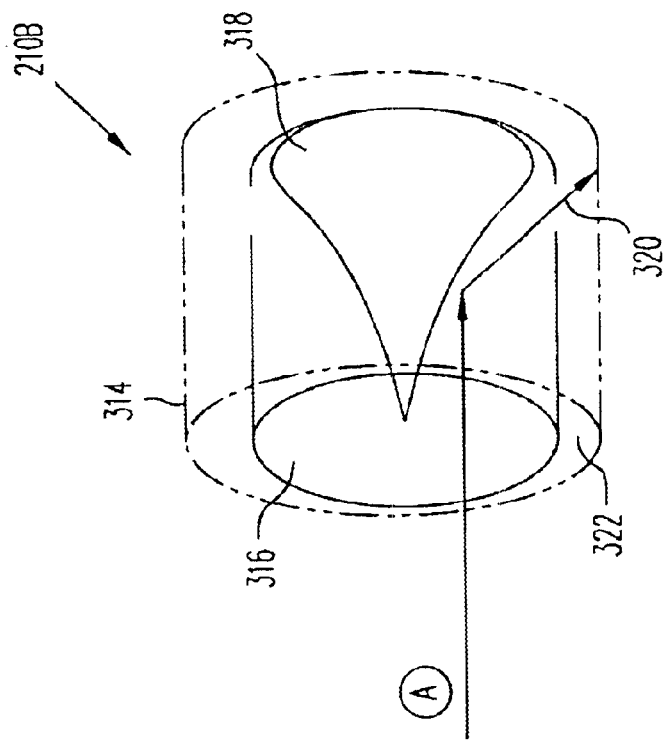
FIGS. 3A, 3B, 3C and 3D are sketches illustrating alternative implementations of the light trap of FIG. 2.
Figure 3A:
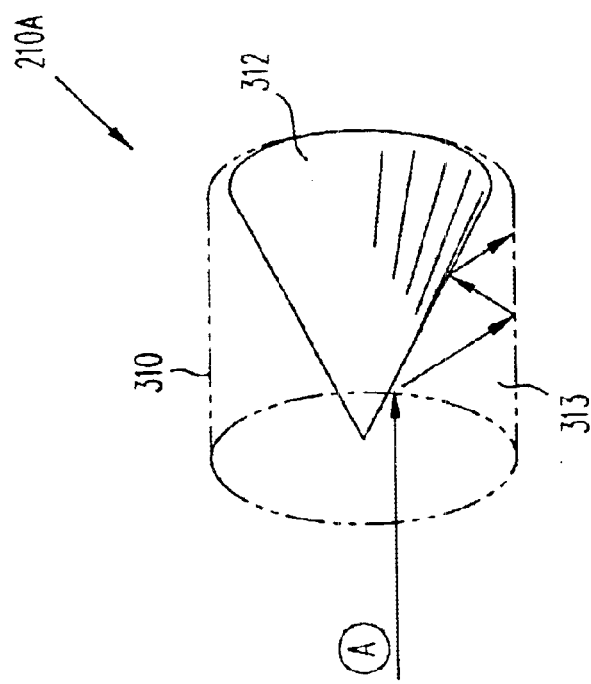
Figure 3D:
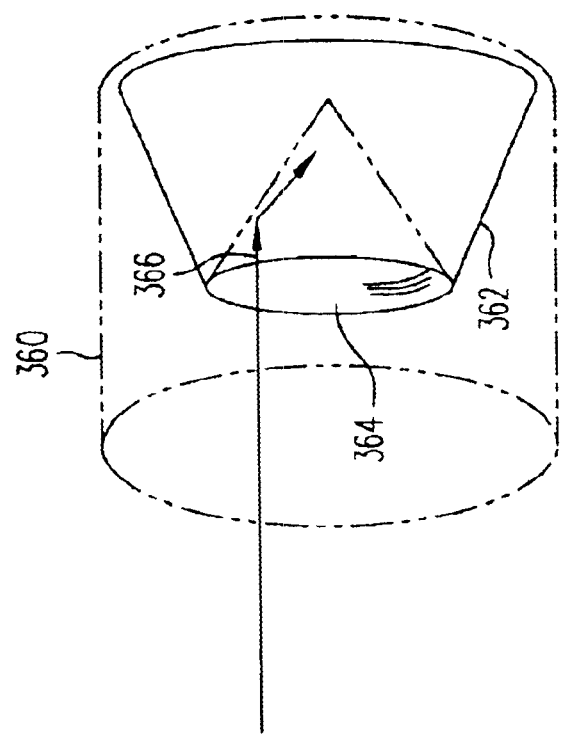
Figure 3C:
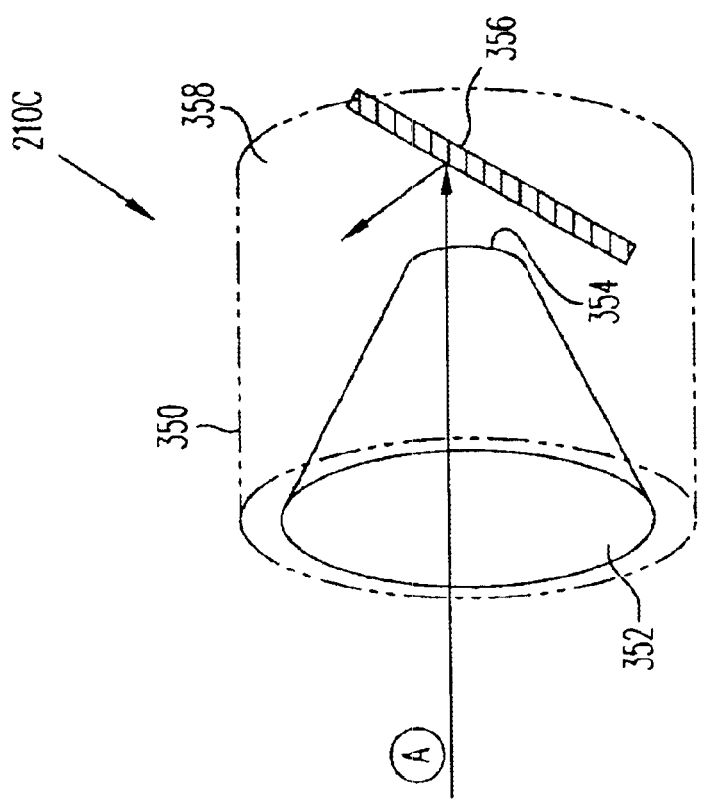

Turning now to FIG. 3C, a further embodiment of light trap 210C is shown. In the embodiment of FIG. 3C, light trap 210C includes a cylinder 350 and a cone 352. Cylinder 350 and cone 352 are positioned to leave a chamber 358 between the outer surface of cone 352 and the inner surfaces of cylinder 350.

In this embodiment, the base of cone 352 faces the source of extraneous light and acts to gather the extraneous light. The extraneous light passes through opening 354 in cone 352. Extraneous light is reflected from surface 356. Surface 356 is angled to reflect the light away from opening 354. In this way, the extraneous light is diverted into chamber 358. Preferably, the inner surfaces of chamber 358 are made of a light absorptive material. The extraneous light is dissipated within chamber 358 without any noticeable reflection back towards mirror 110 and does not interfere with the operation of AOI system 200.

In the embodiment of FIG. 3D, a cone 362 is positioned within cylinder 360. The top of the cone has an opening therein, exposing interior walls. The opening within cone 362 forms a cavity 364. Angled walls 366 within cavity 364 ensure that extraneous light is reflected inwards into the cavity. It is preferable the that angled walls 366 are made of light absorbing material such that light reflected into cavity 364 is quickly dissipated.

Figure 4A:
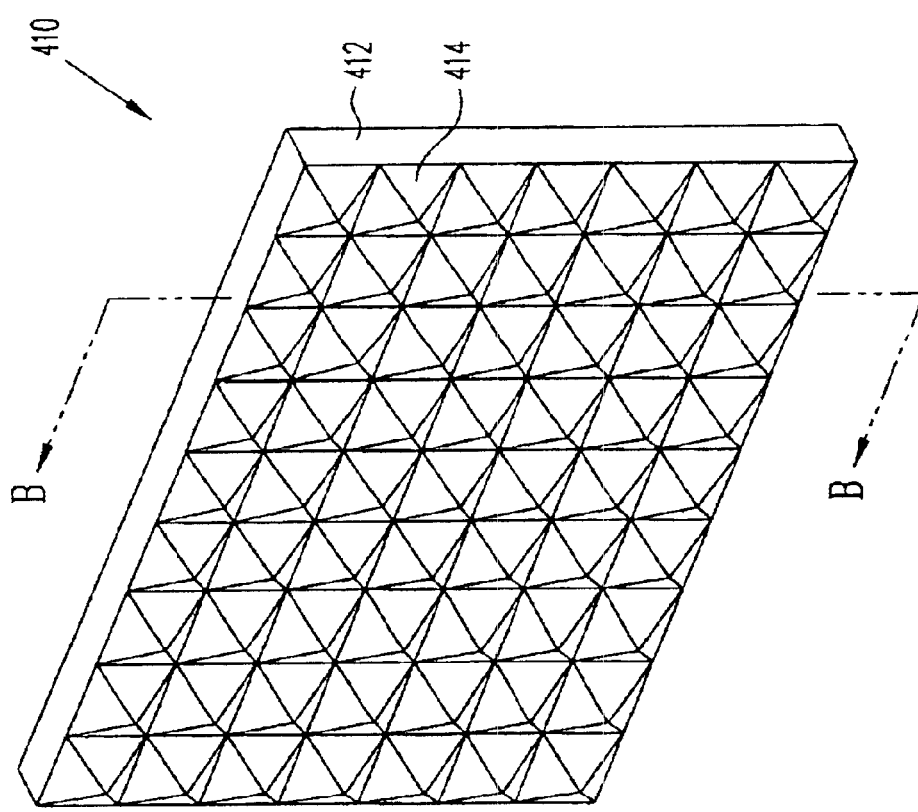
FIG. 4A is a sketch illustrating an alternative implementation of the light trap of FIG. 2.
Figure 4B:
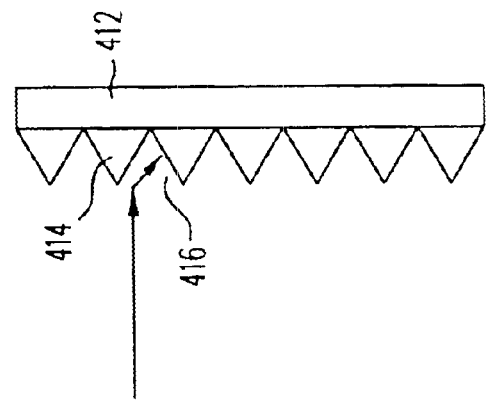
FIG. 4B is a sketch illustrating the light trap of FIG. 4A in cross section along the line B—B.

FIG. 4 shows an alternative embodiment of the light trap. Here, light trap 410 is shown with a plurality of cavities 416 for absorbing extraneous light. The cavities 416 are formed from a plurality of pyramids 414 on a flat surface 412. The outer surfaces of the pyramids 414 are preferably a light absorbing material. Any light reflected from the outer surfaces is diverted into the cavities 416 formed between adjacent pyramids and dissipated.

With the light trap installed, the image formed by camera 112 has drastically improved contrast, sharpness and definition because there is less extraneous light to interfere with the light reflected from the object being inspected.

Having described one embodiment, numerous alternative embodiments or variations might be made. For example, in the preferred embodiment, the components of the light trap were made with black anodized aluminum. Other non-reflective materials might be suitable, such as flat black or painted plastic or other flat black surfaces.

Also, the illustrations show direct paths taken by light. It should be appreciated that light can be bent in space by mirrors or in optical fibers or optical wave-guides. Though straight-line paths are shown for the light, it is possible that the light might not travel in a straight line if mirrors or other light bending devices are used. However, the components might still be "facing" each other in an optical sense despite the fact that the path of the light has been diverted.

As another example, it should be noted that the light trap of the invention included an angled surface that diverted extraneous light into a cavity. For example, the outer surfaces of cones 312 (FIG. 3A) and 318 (FIG. 3B) and angled surface 356 (FIG. 3C) are all angled relative to the direction A in which the extraneous light impinges. These angled surfaces divert light so that it does not reflect back towards mirror 110 where it might interfere with the operation of AOI system 200. In the above-described embodiments, the angled surfaces are made of absorptive material. However, it is not necessary that the angled surfaces be absorptive. Even if the angled surfaces are not absorptive, the extraneous light would dissipate in the chambers 313 (FIG. 3A), 322 (FIG. 3B) or 358 (FIG. 3C).

It should also be appreciated that other shapes of chambers could be formed. And, the angled surface might be given any of a very large number of shapes and still perform the function of directing the incident light away from the opening that leads back to the beam splitter 108.

Therefore, the invention should be limited only by the spirit and scope of the appended claims.

What is claimed is:

1. An optical inspection system comprising:
a) a beam splitter having at least a first, second and third ports;
b) a source of illumination connected to a first port of the beam splitter;
c) a camera connected to a second port of the beam splitter;
d) an inspection area facing the third port of the beam splitter; and
e) a light trap receiving extraneous light from the beam splitter, the light trap having comprising a wall surrounding an angled surface and an opening into a cavity, configured such that a portion of the extraneous light impinging on the angled surface is diverted through the opening into the cavity.

2. The optical inspection system of claim 1 wherein the wall has a cylindrical shape.

3. The optical inspection system of claim 1 wherein the angled surface is parabolic.

4. The optical inspection system of claim 1 wherein the extraneous light comprises light from the source of illumination transmitted through the beam splitter without reflection at the beam splitter.

5. The optical inspection system of claim 1 wherein the angled surface is made of light absorbing material.

6. The optical inspection system of claim 1 wherein the wall comprises light absorbing material.

7. The optical inspection system of claim 1 wherein the wall comprises anodized aluminum.

8. The optical inspection system of claim 1 wherein the angled surface is made of a reflective material.

9. The optical inspection system of claim 1 wherein the light trap comprises a plurality of angled surfaces and a plurality of cavities.

10. An optical inspection system comprising:
a) a source of illumination emitting light in a first direction;
b) a mirror having a reflective surface positioned at an angle transverse to the first direction;
c) an inspection area illuminated by light reflected from the mirror;
d) a camera facing the inspection area; and
e) means for absorbing extraneous light from the source of illumination passing through the mirror, said means being positioned on a side of the mirror opposite the source of illumination and comprising a wall surrounding an angled surface and an opening into a cavity, configured such that a portion of said extraneous light impinging on the angled surface is diverted through said opening into said cavity.

11. The optical inspection system of claim 10 wherein the angled surface is parabolic.

12. The optical inspection system of claim 11 wherein the walls comprises light absorptive material.

13. The optical inspection system of claim 11 wherein the means for absorbing extraneous light comprises a surface having a plurality of projections formed thereon, and wherein the angled surface is one of a plurality of angled surfaces each provided on one of the projections.

14. The optical inspection system of claim 11 wherein the angled surface is a surface of a cone.

15. The optical inspection system of claim 14 wherein the angled surface comprises light absorbing material.

16. The optical inspection system of claim 10 wherein the angled surface comprises a reflective surface.

17. The optical inspection system of claim 10 additionally comprising a computer connected to the camera.

* * * * *